US006547809B1

(12) United States Patent
Cuccia

(10) Patent No.: US 6,547,809 B1
(45) Date of Patent: Apr. 15, 2003

(54) MULTI-FUNCTION CHIROPRACTIC TREATMENT TABLE

(76) Inventor: David F. Cuccia, 227 Jackson Ave., Syosset, NY (US) 11791

( * ) Notice: Subject to any disclaimer, the term of this patent is extended or adjusted under 35 U.S.C. 154(b) by 128 days.

(21) Appl. No.: 09/661,078

(22) Filed: Sep. 13, 2000

Related U.S. Application Data

(60) Provisional application No. 60/153,690, filed on Sep. 14, 1999.

(51) Int. Cl.[7] .................... A61F 5/00

(52) U.S. Cl. .................... 606/242; 606/241; 606/244

(58) Field of Search .................... 606/242, 241, 606/237, 244, 243, 245, 246, 247; 602/32, 33, 34, 35, 36; 5/662, 658; 482/142, 130, 56, 131, 55, 907

(56) References Cited

U.S. PATENT DOCUMENTS

| | | | | | |
|---|---|---|---|---|---|
| 3,568,669 | A | * | 3/1971 | Stites | 128/71 |
| 4,103,681 | A | * | 8/1978 | Shanley | 28/71 |
| 4,546,764 | A | * | 10/1985 | Gerber | 128/33 |
| 4,672,697 | A | * | 6/1987 | Schurch | 5/62 |
| 4,739,749 | A | * | 4/1988 | Lindley | 128/71 |
| 4,915,101 | A | * | 4/1990 | Cuccia | 128/73 |
| 5,176,706 | A | * | 1/1993 | Lee | 606/237 |
| 5,512,040 | A | * | 4/1996 | Mathews | 602/36 |
| 5,840,001 | A | * | 11/1998 | Schedel | 482/142 |
| 5,860,899 | A | * | 1/1999 | Rassman | 482/142 |
| 5,922,011 | A | * | 7/1999 | Cuccia | 606/241 |
| 6,298,854 | B1 | * | 10/2001 | Sundstrom | 128/845 |

* cited by examiner

*Primary Examiner*—John J. Calvert
*Assistant Examiner*—Alissa L. Hoey
(74) *Attorney, Agent, or Firm*—Melvin K. Silverman

(57) ABSTRACT

A rotatable chiropractic treatment table for extension, flexion, traction, distraction and lateral movement of the spine of a patient includes a base adapted to rest upon a floor, and a system support assembly having an upper end and a lower end integrally secured to the base, the support assembly including a pivot axis proximal to upper end. The treatment table also includes a selectable reciprocal extension element having an upper end and a lower end, one end pivotally attached to the system support assembly, the selectable extension elements providing reciprocal movement of the one end relative to an opposite end. The table further includes a rigid support platform having an upper end and a lower end, the platform pivotally secured to the pivot axis of the support assembly and, further, pivotally secured to the one end of the selectable extension element to provide a resultant rotational motion of the support platform. The treatment table yet further includes a body support assembly adjustably positionable relative to the rigid support platform, the assembly having an upper end and a lower end; and an assembly for enabling the patient to remain on the body support assembly during rotational movement.

21 Claims, 9 Drawing Sheets

102

MULTI-FUNCTION CHIROPRACTIC TREATMENT TABLE

REFERENCE TO RELATED APPLICATION

This case corresponds in part to the subject matter of Provisional Application Ser. No. 60/153,690, filed Sep. 14, 1999. The subject matter thereof is incorporated herein by reference.

BACKGROUND OF THE INVENTION

The within invention is an improvement of the inventions of my U.S. Pat. Nos. 4,915,101 (1990) and 5,922,011 (1999).

Numerous devices, including chiropractic, osteopathic, obstetrical, delivery, x-ray and operating tables, which suspend or position a patient in a unique way for some special purpose, are known in the art.

U.S. Pat. No. 4,292,926 (1981) to Krause presents an apparatus for effecting postural treatment of humans in which the patient, while resting face down on a pivoting platform, can vary the position of his arms, adjust his center of gravity while in suspension and, thereby, affect his posture upon the table.

U.S. Pat. No. 4,568,669 (1971) to Stiles discloses a posture board wherein the patient is rotated 180 degrees from an initial upright position on his back to one of complete inversion hanging by the ankles. With the body hanging freely, normal gravitational pull is reversed thus causing a therapeutic effect on bone structure, spinal column, muscles, internal organs and body fluids.

U.S. Pat. No. 4,103,681 (1978) to Shanley similarly discloses a tilting traction apparatus where the patient, again lying on his back, is rotated about a pivot point to treat back injury or postural misalignment.

It is to be appreciated that the success of any device designated to treat lower back dysfunction is in large part dependent on proper positioning of the patient prior to, during, and after treatment. For example, in standard traction therapy, the patient wears a pelvic harness and is positioned supinely (face up) in bed, with the spine slightly flexed and knees bent. Straps or roping which is attached to the harness are then inserted into a pulley mechanism and weights attached at an opposite end, causing a desired pulling/traction effect. Such pulling traction force produces an elongation of the spinal column (distraction) and a reduction in internal intervertebral disc pressure. This creates a vacuum phenomenon inside the disc, which retracts protruded gelatinous material back into its fibrous casing and off of the spinal nerve roots. With the pain gone and the anatomy restored to its natural state, the traction phase of therapy is complete.

An alternate theory for accomplishing the same result is based on extension, rather than flexion of the spine, to achieve reduced intradiscal pressure, while simultaneously anatomically moving nerve roots away from the herniated disc.

While the general principles of flexion and axial traction of the spine are known in the art and have been effected in various strap and/or harness arrangements, either alone or in combination with rotating-pivot type tables as are described above, the inventor has found that both flexion and extension, as well as lateral positioning with traction, can all be beneficial depending upon the patient's particular ailment or condition.

As such, there exists a need for a system which combines varying degrees of both traction or distraction with concomitant patient position flexion, extension, lateral flexion, and or axial spinal positioning. The present invention being both beneficial to the patient and convenient to the doctor, fulfills this need in a variety of ways in that the inventive treatment table not only enables rotation of a patient about a pivot point but, additionally, permits the relative, selectable positioning of the patient's arms, upper torso, legs, lower back, head and shoulders through manual adjustment or an automatic keypad control. The present invention also allows a complete choice as to prone, supine or lateral positioning of the patient prior to treatment. It further enables the doctor to vary the position of the patient prior to and during treatment, and to vary the degree of tractive force applied to the patient by selectably variably rotating the patient platform to increase or decrease the tractional gravitational pull applied through such rotation. There is further provided a "dynamic rotation" into a variable vertical traction position, i.e., the patient stands upright against the table, supported by an adjustable shoulder, arm and hand support and is lifted off the ground, thereby achieving tractional dynamics related to those described above, namely a rapid lengthening of the muscles and longitudinal ligaments of the spine increasing the separation of the intervertebral disc and articular joint spaces. This results in both mobilization of the spine and rapid development through the "disc unloading" of a negative internal disc pressure responsible for causing the vacuum phenomenon for retracting protruding disc material back within the borders of a healthy disc while keeping the patient suspended in mid-air, or while the patient remains standing on a weighted patient platform, utilizing the weight of the lower extremity, the force of gravity, and selected patient anatomical positioning.

My instant invention therefore defines functionally over the structure of my said U.S. Pat. Nos. 4,915,101 and 5,922,011 in the following material respects:

1. Ability to concurrently or sequentially lift and rotate the patient, thus providing various treatment options to the physician, including more effective traction of vertebral segments prior to and during table and patient rotation, thereby reducing stress on articulate vertebral surfaces of the patient and obtaining a generally more ergonomic patient interface.

2. Ability to change radius of lower back support assembly, to effectuate varying degrees of lumbar extension and lumbar support, as well as a general mobilization of the lumbar spine (lower back).

3. Ability to tilt the top or bottom half of the lower back support assembly, allowing a greater range of positions of the patient's lumbar spine, and to increase or decrease the lumbar lordosis.

4. Enhanced patient safety, through the use of selectable patient strapping and other support means, including a thoracic harness, abdominal strapping, overhead wrist strapping and use of arm support assemblies.

5. Ability to rotate the leg support assembly side to side allowing lateral mobilization and enhanced stretching of the muscles and ligaments of the spine.

SUMMARY OF THE INVENTION

A rotatable treatment table for extension, flexion, traction, distraction and lateral movement of the spine of a patient is provided. The table more particularly includes a base adapted to rest upon a floor, and system support means having an upper end and a lower end integrally secured to said base, said support means including a pivot axis proximal to said upper end thereof. The treatment table also includes means for selectable reciprocal extension having an upper end and a lower end, one end pivotally attached to said system support means, said selectable extension means providing reciprocal movement of said one end relative to an opposite end thereof. The table further includes a rigid support platform having an upper end and a lower end, said platform pivotally secured to said pivot axis of said support means and, further, pivotally secured to said one end of said selectable extension means, thereby providing a resultant rotational motion of the support platform. The treatment table yet further includes a body support assembly adjustably positionable relative to said rigid support platform, said assembly having an upper end and a lower end; and means for enabling said patient to remain on said body support assembly during rotational movement thereof.

A principal object of the invention is to provide a multipurpose table to effectuate flexion, extension, traction, lateral movement and distraction of the spine, as may be required in the treatment of spinal disorders and/or maintenance of proper human posture, in such a manner that the relative positions of the patient's arms, legs, lower back, head and shoulders can be varied.

Another object of the invention is to provide a multipurpose rotatable traction/treatment table permitting patient rotation and dynamic lifting of a patient while standing, concurrently with selective patient body positionings as may be required in the treatment of disc herniations and other disorders and/or maintenance of proper human posture.

Yet another object of the invention to provide a treatment table having a range of motion from zero to at least ninety degrees and, within that range, which can pivot from zero to at least ninety degrees, thereby providing the ability to achieve spinal positioning including spinal flexion, extension, lateral flexion, and axial spinal positioning and traction in the absence of a lower leg support assembly enabled by inherent torso support and placement of the human body at or near its center of gravity at the lower back support assembly.

A still further object is to provide a table which having a variety of pneumatic and other adjustments to permit that patients of widely disparate age, height and weight to be accommodated, without requirement of extended physician set up time.

A further object of the invention is to provide a multipurpose table that is simple to operate, weighted and designed for safety so as not to tip, and constructed of quality materials.

A yet further object is to provide a system in which the position of the upper torso support assembly may be varied relative to the lower back support assembly.

It is another object to provide a system than can concurrently or sequentially lift and/or rotate the patient, this providing various treatment options to the physician, including more effective and safer traction of vertebral segments by inducing less stress on articulate vertebral surfaces of patient, and a generally more ergonomic patient interface.

Another use of the table is that of enabling the patient to exercise and strengthen the spine and related musculature to maintain and enhance the health thereof.

It is another object to provide a treatment table capable of easy and variable patient means to remain on body support platform during "dynamic" liftoff including overhead or underarm patient hand gripping means and overhead thoracic harness strapping means.

It is a further object to effectuate flexion, extension, lateral flexion, and axial spinal positioning through easily accessed patient activated control switches to allow patient participation in treatment, improved patient safety, and better patient compliance.

Other objects and advantages of the invention will become apparent from the Detailed Description of the Invention, the Drawings, and Claims appended herewith.

DETAILED DESCRIPTION OF THE INVENTION

Figure 1:
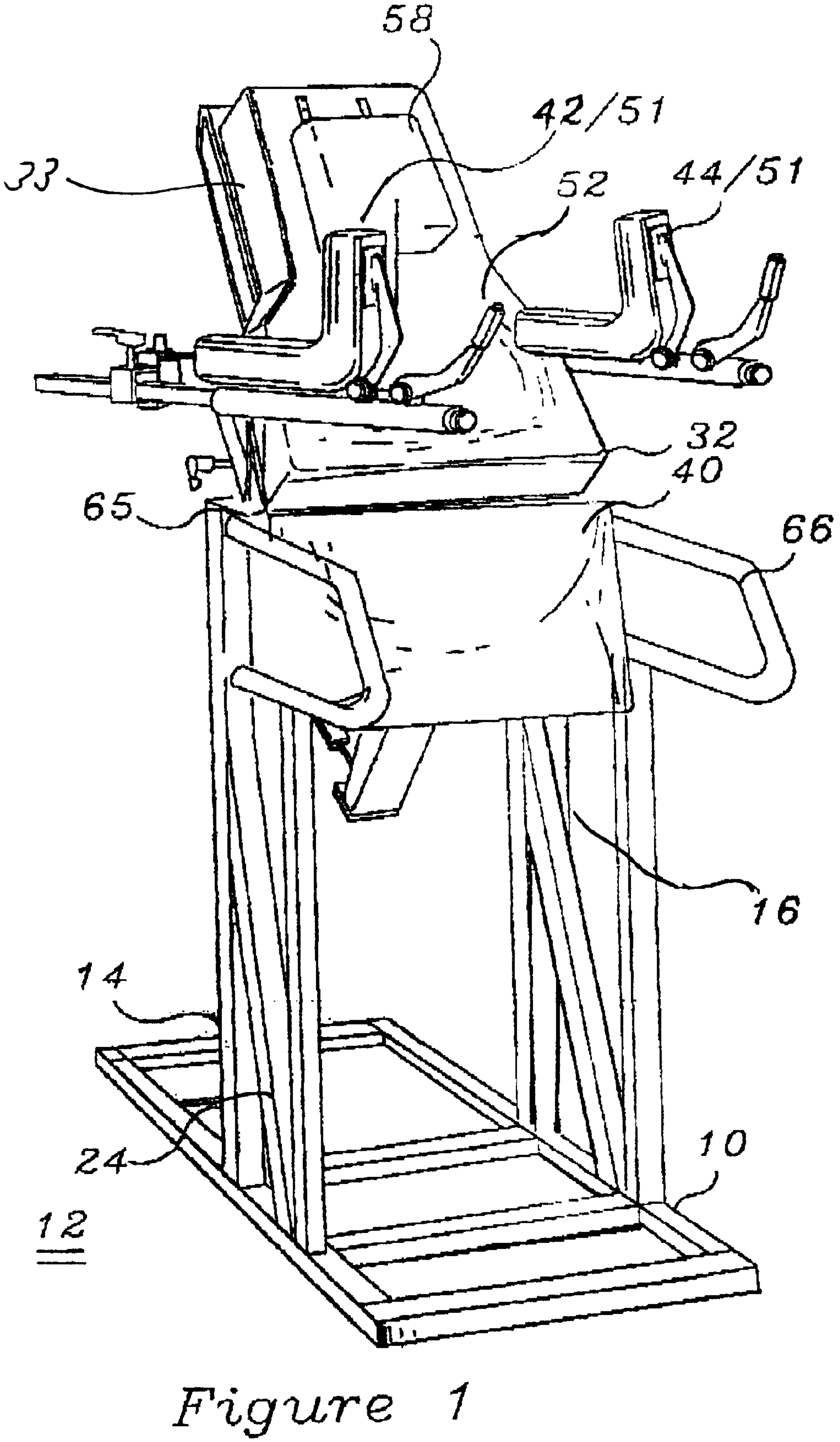
FIG. 1 is a front perspective view of a first embodiment of the inventive chiropractic table.

With reference to the views of FIGS. 1 through 4, the present chiropractic treatment table for effecting extension, flexion, traction and distraction of the spine of a patient, may be seen to include a base 10 adapted to rest upon a floor 12, in a typical treatment room of a chiropractor, physical therapist, or other health professionals involved in physical medicine. The chiropractic table may be seen to optionally include a pair of extensible elevation means 14 and 16, which may be a part of system support means 24. Means 14 and 16 thereby accommodate patients of various heights and can assist in the positioning of patients on the table.

Figure 2:
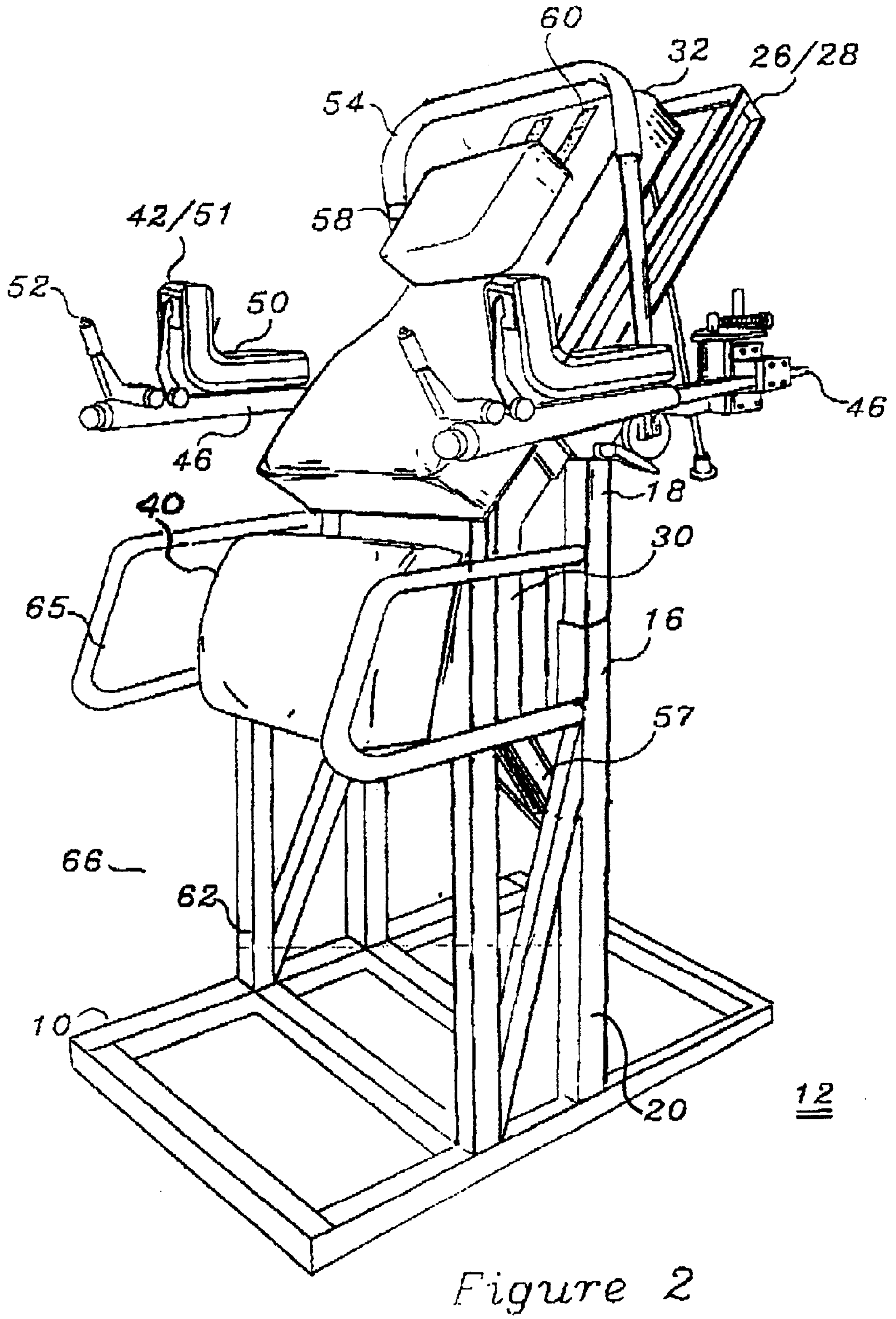
FIG. 2 is a front diagonal perspective view thereof.
Figure 3:
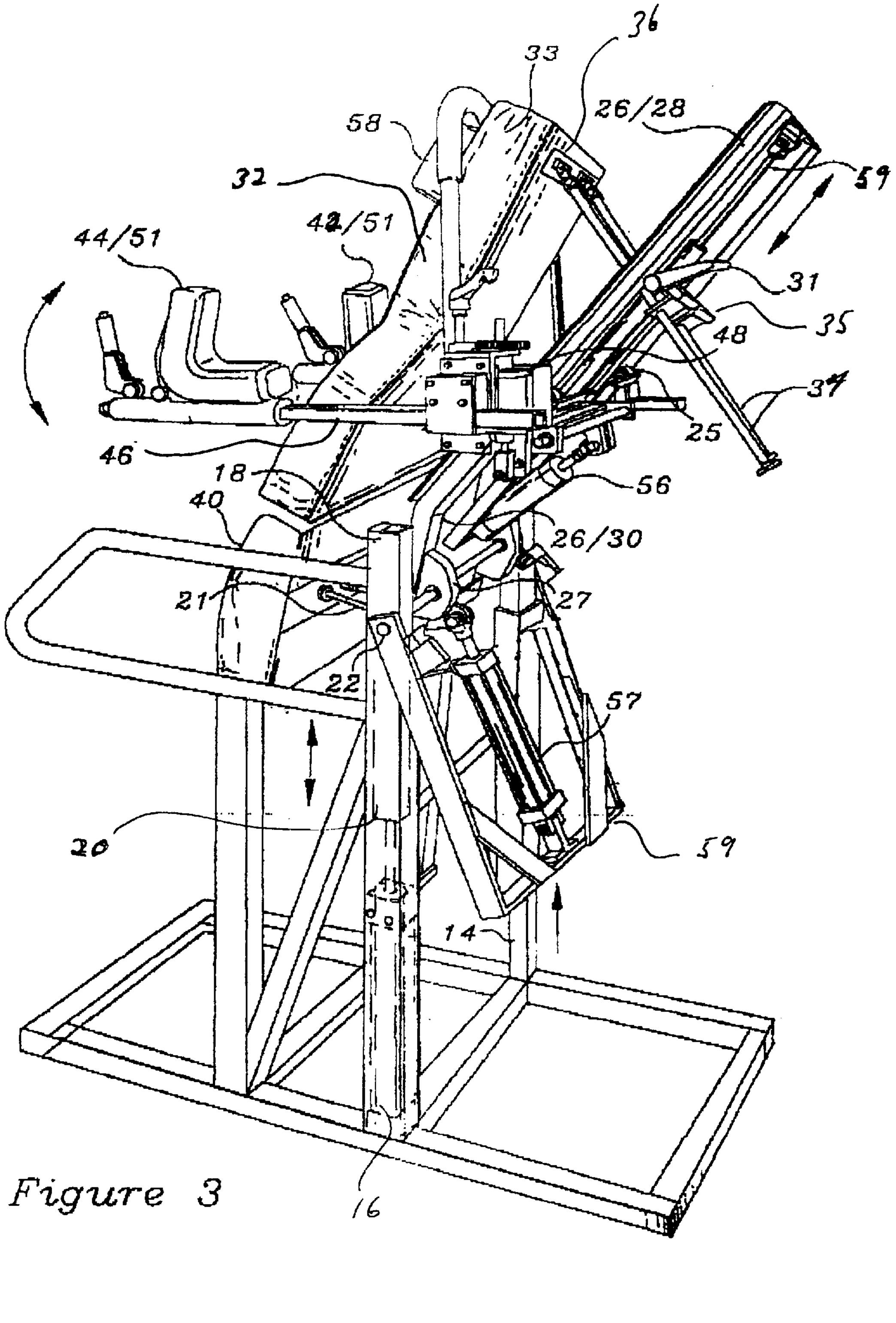
FIG. 3 is a side diagonal perspective view of the inventive table.

With reference to FIG. 3, it may be seen that the extensible elevation means 14 and 16 (if they are used) preferably comprise extensible hydraulic pistons, each including an upper end 18 and a lower end 20. Said upper end 18 includes a transverse horizontal pivot axis 22 which thereby connects thru said upper ends 18 of each of the elevation means 14 and 16. As may be appreciated in the views of FIGS. 1 through 3, the lower ends 20 of each of the vertical elevation means are also a part of system support means 24 and may be integrally secured to said base 10 through the use of a diagonal support and/or other means not shown in the drawings.

The instant multi-purpose treatment table further includes a rigid support platform 26 (see FIGS. 2 and 3) having an upper part 28 and a lower part 30. Said lower part 30 of rigid support platform 26 is secured to a pivot block 27 (see FIG. 3) which is rotatable upon pivot axis 22 at the approximate mid-point of lower part 30 of platform 26. As may be further noted, said upper part 28 defines a plane which is preferably tilted convexly (see FIG. 2) and at an angle of about thirty degrees relative to a plane defined by said lower part 30 of the rigid support platform 26. Such an angle is necessary in that it allows the patient's upper body to be ergonomically supported by a body support assembly 32, permitting the back to extend convexly and backward at variable selectable angles relative to base 10. Support assembly 32 is mounted upon said upper part 28 of said rigid support platform 26 includes means 31, 34, and 35 for selectable adjustment of a the angle of an upper area 33 of assembly 32 relative to a plane defined by said upper part 28 of support platform 26. This assembly 32 may include a protractor to more accurately to better measure said angle. Said body support assembly may or may not be divided into, or may or may not include, moveable sections with hydraulic or pneumatic pistons or other means for elevation and de-elevation of the body support assembly 32. Said assembly may contain an integral air bladder for additional immobilization.

With reference to FIGS. 1 to 4, the system may also be seen to optionally include a pair of positionally adjustable arm support means 42 and 44 which are located proximally to the sides of the body support assembly 32. As is set forth below, said arm support means include a selectably adjustable rear portion 46 which is secured to said upper part 28 of the rigid support platform 26. Said arm support means 42 and 44 include (i) a substantially horizontal arm rests 50; (ii) a chest and shoulder support 51 situated posteriorly and angled inwardly in a patient direction from said arm rest; and (iii) a tilted hand grip 52 depending integrally upwardly and inwardly, proximally to said chest and shoulder supports 51. See FIG. 4.

With further reference to the figures, the present treatment table may be seen to optionally include a lumbar and buttock support assembly 40, which may or may not be integral with said body support assembly 32. Assembly 40 is connected to telescoping rods 21 (see FIG. 3) or other means which provide means for elevation and de-elevation thereof. Said assembly may include an internal air cushion in the form of an inflatable air bladder, for added support and tissue mobilization. The same is true of the upper torso support assembly.

The table may also include a head rest 58 (see FIGS. 2 and 3), as a part of the body support assembly 32, or separate therefrom, which is positionally adjustable with or without Velcro tracks 60 upon the body support assembly 32.

With reference to FIGS. 2 and 3, the present chiropractic table may be seen to further include means for selectable reciprocal extension, i.e., an electromechanical linear actuator or an extensible hydraulic or pneumatic piston 57, mounted within a frame 59, which enables rotation of said rigid support platform 26 upon said horizontal pivot axis 22 by rotation of pivot block 27 to which platform 26 is secured. Frame 59 may include a protractor to better measure the degree of rotation. It is, accordingly, to be appreciated that extensible piston 57 facilitates a central function of the chiropractic table, i.e., the rotation of all assemblies attached to the rigid support platform 26, including body support assembly 32, the lumbar support assembly 40, and the adjustable arm support means 42, all through the use of a single control assembly, namely, extensible piston 57 of frame 59.

Figure 4:
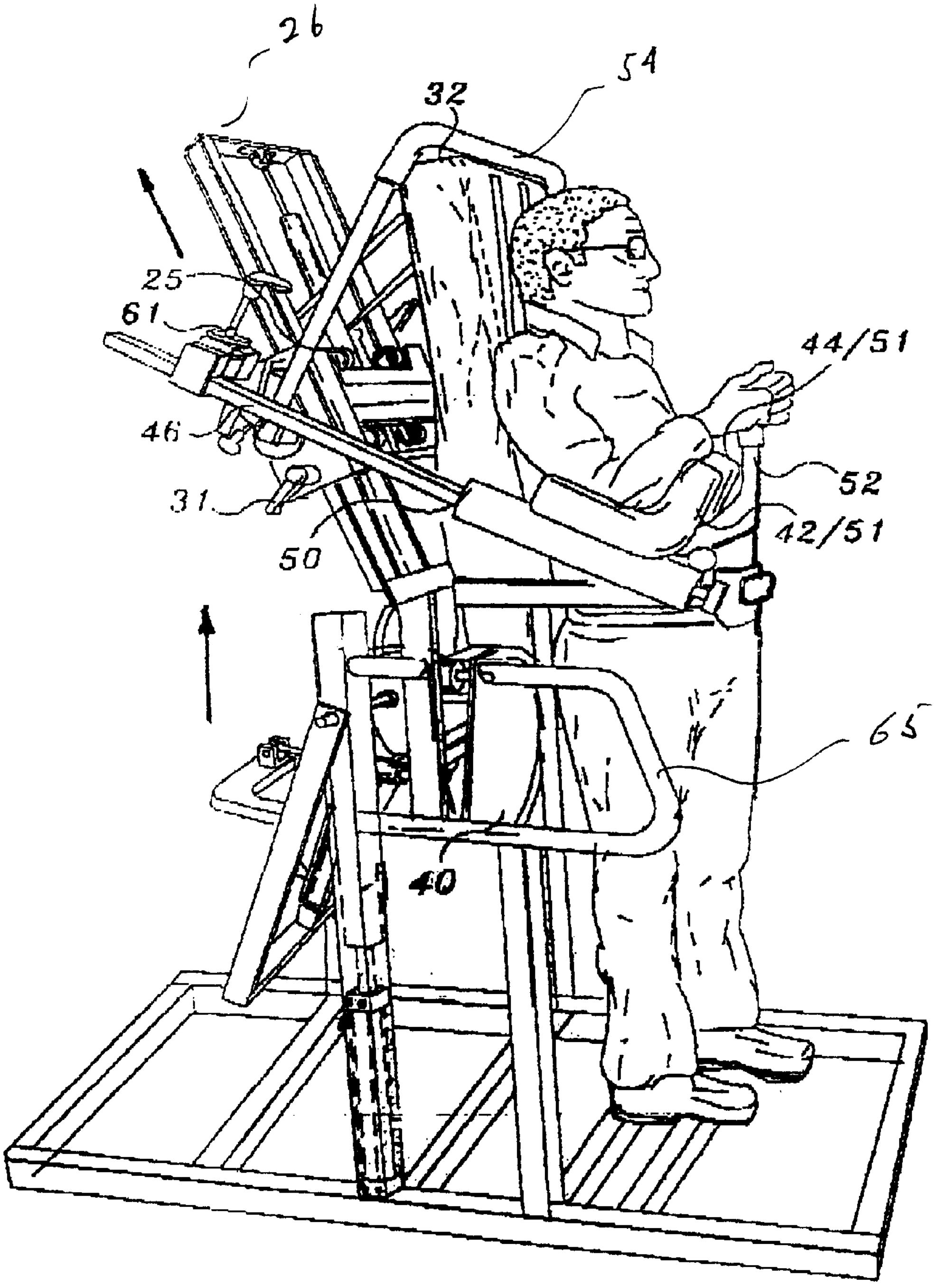
FIG. 4 is an operational view of the invention.

Shown in FIG. 4 is a perspective view of a patient making use of shoulder and chest supports 42 and 44 and further showing an embodiment of the invention that includes lower hand grips 52 which, together with the entire assembly, provides safer patient restraint and/or securement while satisfying the patient's instinctive need to hold himself in position.

Figure 5:
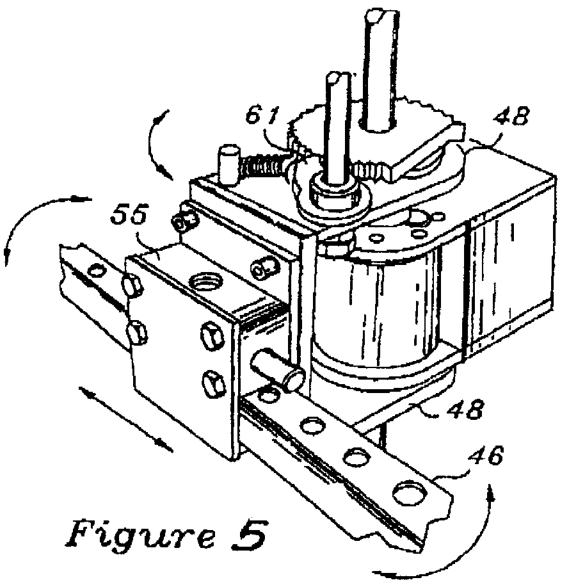
FIG. 5 is an enlarged perspective view of an arm positioning assembly associated with the invention.

Shown in FIG. 5 is the rear of arm support assemblies 42 and 44, namely, a rotation assembly 48, selectable adjustment means 46, and guide locking means 55. Also shown is arm support locking means 61. The degrees of freedom effectuated by the assemblies shown in FIG. 5 are indicated by the linear and curved arrows therein.

Figure 6:
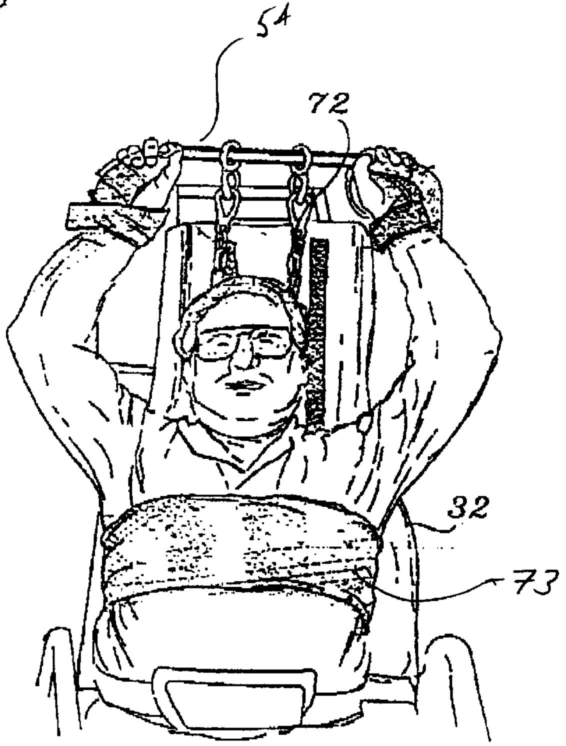
FIG. 6 shows a second embodiment of the invention involved in the use of thoracic traction means and overhead arm gripping means.

In FIG. 6 is shown a further use of the invention which includes therein thoracic traction means 72 which is attached to transverse overhead arm gripping means 54. Also shown in FIG. 6 is a harness 73 which may be used secure and stabilize the patient relative to body support assembly 32, particularly during rotational movement thereof.

Figure 7:
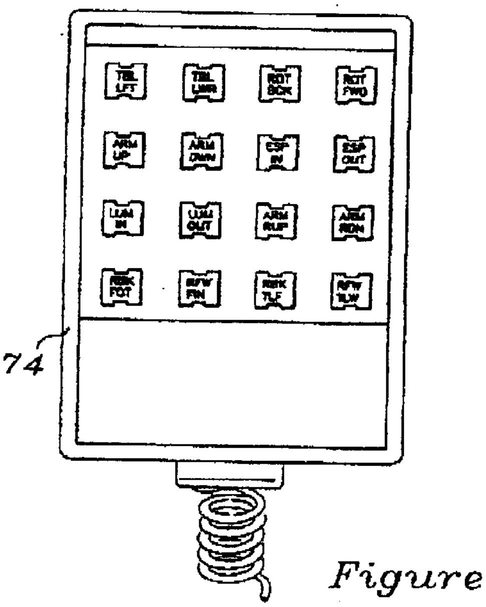
FIG. 7 is a plan view of a system keypad control.

FIG. 7 illustrates a system keypad 74 for use by the doctor which includes the following function buttons:

| | | |
|---|---|---|
| 1. TBL LFT | = | Table Lift. |
| 2. TBL LWR | = | Table Lower. |
| 3. ROT BACK | = | Rotate Table Back. |
| 4. ROT FWD | = | Rotate Table Forward. |
| 5. ARM UP | = | Translational Arm Height Up. |
| 6. ARM DWN | = | Translational Arm Height Down. |
| 7. OPEN | | |
| 8. OPEN | | |
| 9. ARM R. UP | = | Arm Rotate Up. |
| 10. ARM R. DOWN | = | Arm Rotate Down. |
| 11. LUM IN | = | Lumbar In |
| 12. LUM OUT | = | Lumbar Out |
| 13. OPEN | | |
| 14. OPEN | | |
| 15. RBK TL | = | Rotate Table Back with Table Lift. |
| 16. RFW TLW | = | Rotate Table Forward with Table and Lower Table. |
| 17. SAFETY ON AND OFF | = | A safety on and off button is included which stops pneumatic/hydraulic piston and ceases all table movement. |

As a safety measure, button 17 above may also be incorporated into overhead gripping means 54 or into hand grips 52 (see FIGS. 1 and 2), with optional patient control of other functions.

With reference to FIGS. 8 thru 11, there is shown a preferred embodiment of the invention which, more particularly, includes a base 100 adapted to rest upon a floor 102. Said embodiment of the invention further includes a system support means 104 which, as may be noted in the rear view of FIG. 10, includes two vertical members having a pivot axis 106 secured between upper ends 108 thereof.

The system of FIGS. 8 thru 11 further includes means for selectable reciprocal extension 110 in the nature of an electromechanical linear actuate or a piston 112 and cylinder 113 in which piston 112 thereof is attached at pivot point 114 to a pivot block 116. Associated with reciprocal extension means 110 is a linear rigid member 118 having a lower end 120 which is hinged to a lower end 121 of said reciprocal extension means 110. An upper end 122 of said rigid member 118 is rotationally secured to said pivot axis means 106. See FIG. 11. As may be further noted in the views of FIGS. 8 and 9, there is provided a rigid support platform 124 having an upper end 126 and a lower end 128. Said platform is pivotally secured to said pivot axis 106 thru the connection of pivot block 116 to said lower area 128 of the support platform 124. It is to be appreciated that through the co-action of reciprocal extension means 110 and rigid member 118 relative to pivot axis 106 and pivot block 116 (to which piston 112 of extension means 110 is also secured), the entire rigid support platform 124 may be rotated relative to pivot axis 106. Typically, such a rotation can be effected manually by the chiropractic physician in that, when a patient is positioned upon body support assembly 130, the center of gravity of the present chiropractic table with the patient therein will be located closely enough to pivot axis 106 to permit rotation of support platform 124 and with it, body support assembly 130, with a minimal effort on the part of the physician.

Figure 8:
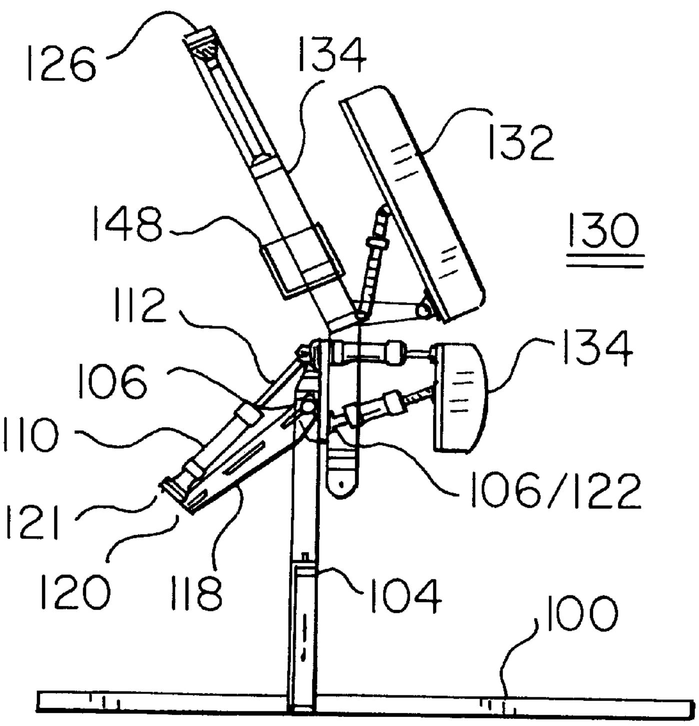
FIG. 8 is a side plan view of a further embodiment of the invention in which an extensible pneumatic piston is used to provide independent articulation and movement of a lumbar assembly relative to the body support assembly of the treatment table.
Figure 9:
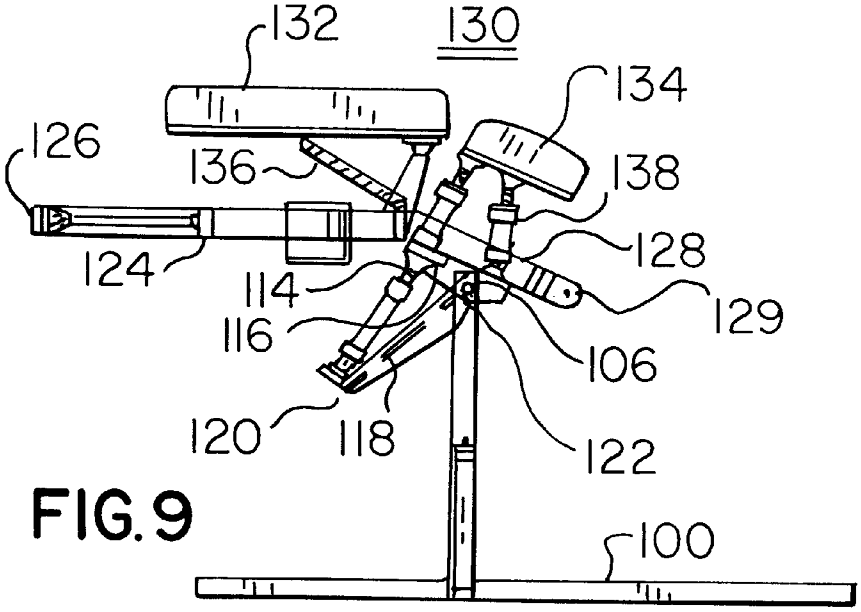
FIG. 9 is a plan view, similar to that of FIG. 8, however showing rotation of the rigid support platform relative to the pivot axis of the system support means.
Figure 10:
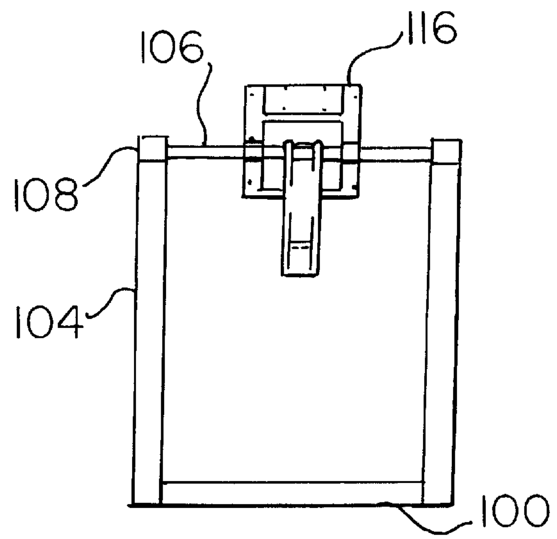
FIG. 10 is a rear plan view of FIG. 9.

As may be further noted in FIGS. 8 and 9, the body support assembly 130 includes an upper portion 132 and a contoured lumbar and buttock support 134. Therein, upper portion 132 is angularly and translationally adjustable relative to rigid support platform 124 by scissors arms 136. Therein, the distance of upper portion 132 relative to support platform 124 may be altered, as may be the angle of the plane of said portion 132 relative to platform 124.

Figure 11:
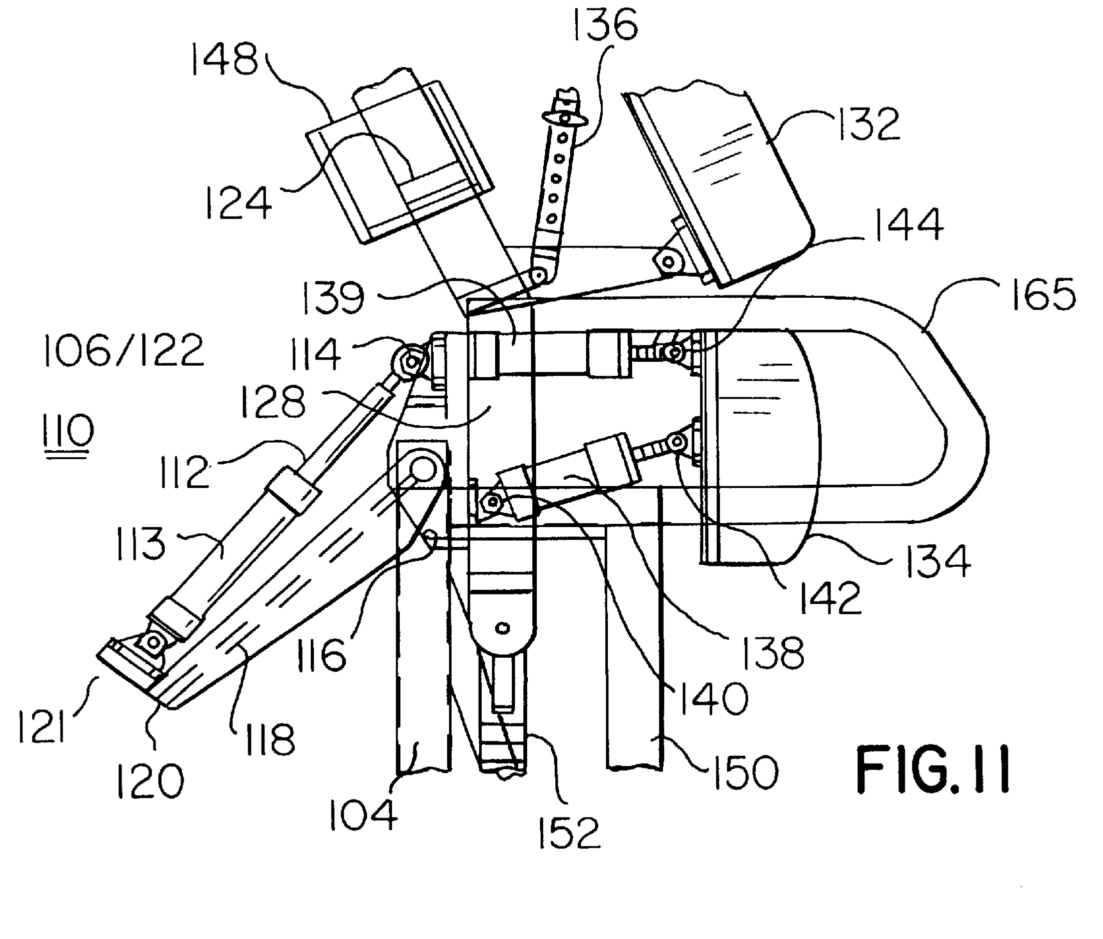
FIG. 11 is an enlarged view of the lumbar cushion and extensible piston means in the view of FIG. 8.

Yet further shown in the embodiments of FIGS. 8 thru 11 is the use of airfoil pistons 138 and 139, both of which are secured, at the proximal ends thereof, to pivot block 116 of rigid support platform 124. It is, however, to be noted that lower airfoil piston 138 is pivotally secured to lower portion 128 at a pivot point 140, while upper airfoil piston 139 is rigidly secured to block 116. It is also noted that lumbar and buttock support 134 is pivotally attached to distal ends of airfoil pistons 138 and 139 and points 142 and 44 respectively. As such, lumbar support 134 may be readily tilted relative to pivot point 140 to provide independent articulation, movement, and adjustment of the effective radius of support 134 relative to lower portion 138 of platform 124. Further shown in FIG. 11 are side gripping means 165.

At the upper center of FIG. 11 is shown arm adjustment means 148 (see also FIG. 12) which enables translation movement of arm assemblies change to accommodate patients of different heights. FIG. 11 also indicates that multiple vertical elements, such as vertical members 150 may be employed, in combination with said vertical members 104, to provide a more stable system support means. At the bottom of FIG. 11 is shown a lower support platform extension 152 which may be used to shorten or extend the length of lower portion 128 of the support platform 124. Further shown in FIG. 11 are side gripping means 165.

Figure 12:
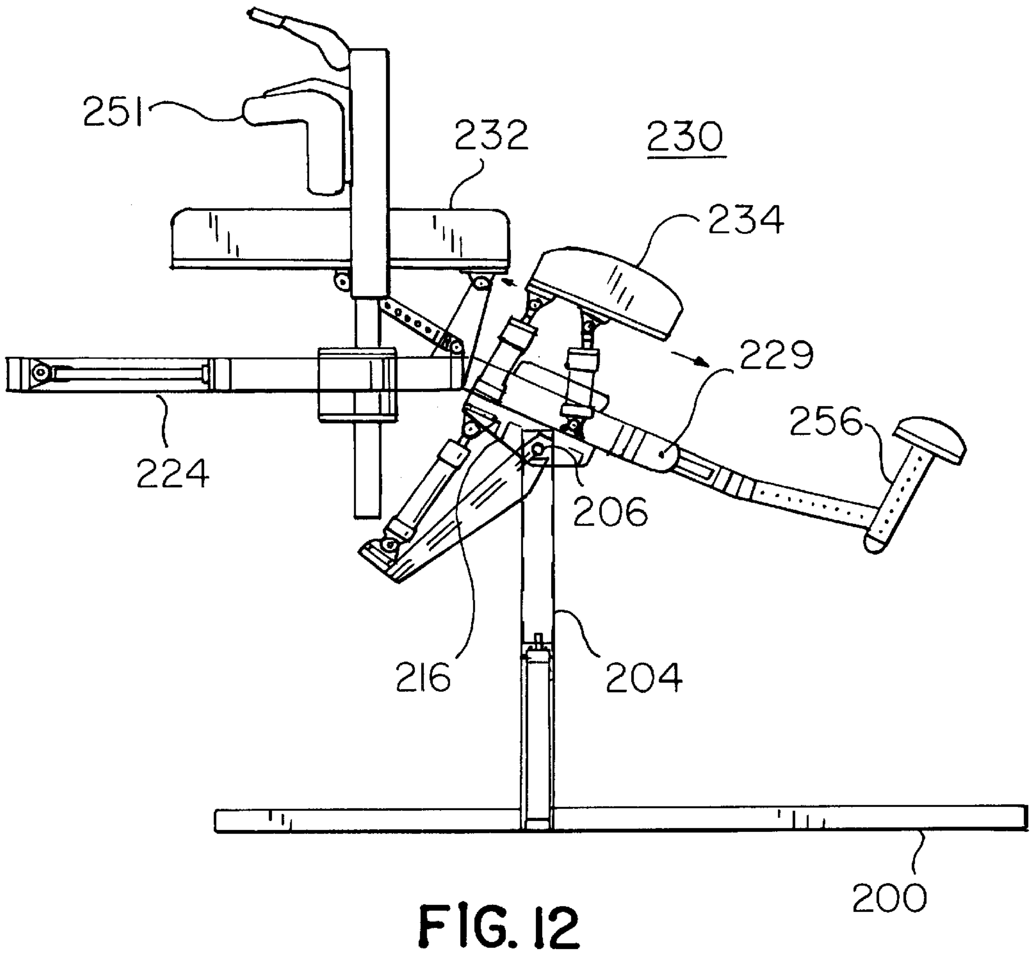
FIGS. 12 and 13 are plan views corresponding to the views of FIGS. 9 and 10 however showing the use of a motor output to rotate the horizontal pivot axis as a fulcrum of the support platform.
Figure 13:
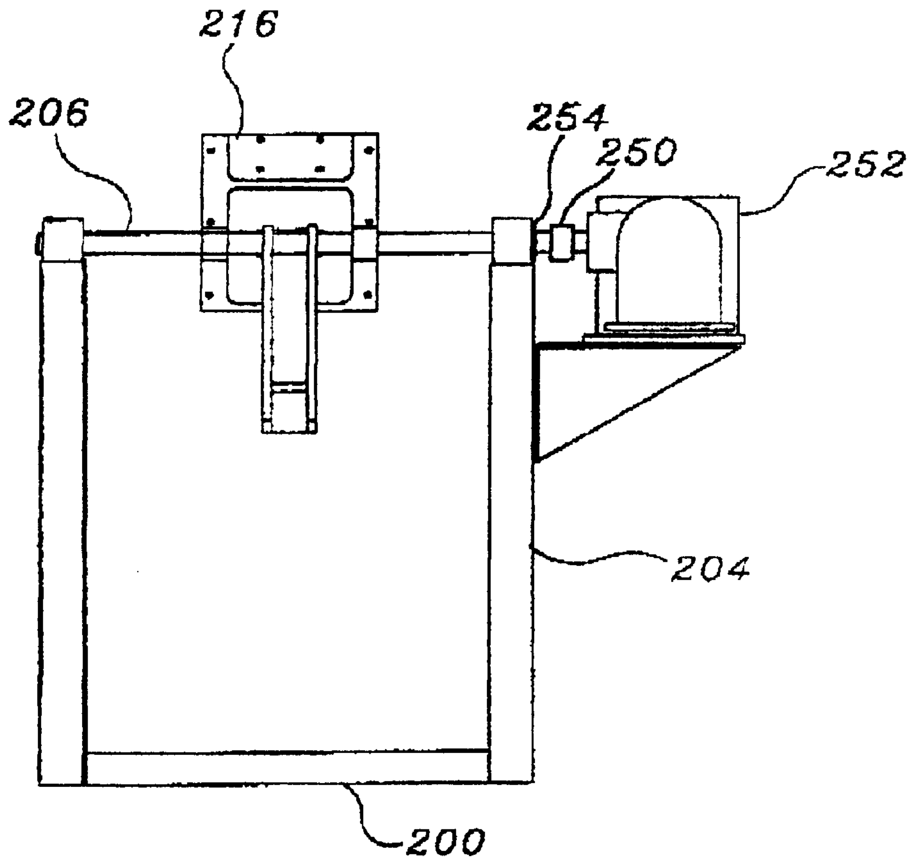

In the views of FIGS. 12 and 13 is shown a further embodiment of the invention in which a fulcrum axis 206 is fixed relative to a body support assembly 224 and pivot block 216. In this embodiment, the entire support platform is rigidly fixed to the fulcrum 206 such that through the use of an output 250 from a motor or other electromechanical actuator 252, a gear 254, or mechanically equivalent means, may be used to effect a tilting of fulcrum 206 and, therewith, support platform 224 and its associated body assembly 230. In all other respects, the embodiment of FIGS. 12 and 13 follows that of the embodiments of FIGS. 8 through 11, however, shown in FIG. 12 is an optional element, applicable to both assemblies, namely, a leg support assembly 256. Such leg and calf support assemblies affords a variety of therapeutic effects upon the spine of the patient and, particularly, in the context of (i) dynamic rotation of the patient off the ground, (ii) selectable positional adjustment of the body platform relative to the base, and (iii) in the ability to more easily position either or both back assembly 232 and lumbar support 234 relative to a patient's center of gravity.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention.

I claim:

1. A rotatable treatment table for extension, flexion, traction, distraction, and lateral movement of the spine of a patient, the table comprising:

(a) a base adapted to rest upon a floor;

(b) system support means having an upper end and a lower end integrally secured to said base, said support means including a pivot axis proximal to said upper end thereof;

(c) means for selectable reciprocal extension having an upper end and a lower end, one end pivotally attached to said system support means, said selectable extension means providing reciprocal movement of said one end relative to an opposite end thereof;

(d) a rigid support platform having a lower part and an upper part, said platform pivotally secured to said pivot axis of said system support means and, further, pivotally secured to said one end of said selectable extension means, thereby providing a resultant rotational motion of said support platform;

(e) a body support assembly adjustably positionable relative to said rigid support platform, said assembly having an upper end and a lower end; and (f) means for enabling said patient to remain on said body support assembly during rotational movement thereof.

2. The system as recited in claim 1 in which said body support assembly further comprises:

a contoured lumbar and buttock support in which a center of gravity of a patient is within a longitudinal dimension of said lower end of said body support assembly.

3. The table as recited in claim 2 further comprising:

means for adjusting a radius of said contoured lumbar and buttock support above a plane of an upper part of said body support assembly to thereby impart a selectable radius to said lumbar support, thereby providing correction of anatomical curvature of the lower back.

4. The table as recited in claim 2 in which:

said body support assembly comprises a torso support assembly and a head support assembly.

5. The table as recited in claim 2 further comprising:

a head assembly mounted to said body support assembly above said lumbar support, and postionally adjustable in a plane normal to said assembly within a range extending above and below a plane thereof.

6. The treatment table as recited in claim 2 further comprising patient gripping means transversely dependent from said rigid support platform.

7. The table as recited in claim 2 further comprising:

a head assembly mounted to said body support assembly above said lumbar support, and postionally adjustable in a plane normal to said assembly within a range extending above and below a plane thereof.

8. The treatment table as recited in claim 2 further comprising patient gripping means transversely dependent from said system support means.

9. The table as recited in claim 1 further comprising:

a lumbar support assembly separated from said body support assembly; and means for independent articulation and movement of said lumbar assembly in a plane either above, or tilted relative to proximal portions of said body support assembly.

10. The table as recited in claim 9 further comprising:

a leg support assembly transversely mounted to said rigid platform, said assembly comprising a cushion positionally adjustable relative to a plane normal to said platform and having a range extending below said plane in which the curvature of the lower body of a patient, beneath the center of gravity thereof, may be thereby regulated, whereby a variety of therapeutic effects upon the spine of a patient may be accomplished through dynamic rotation thereof off of the ground, selectable positional adjustment of said body platform relative to said base, and change in position of either or both said back assembly and said leg support assembly relative to the patient center of gravity.

11. The table as recited in claim 10 further comprising:

means for permitting lateral movement of said leg support assembly relative to a longitudinal axis of said body support platform.

12. The treatment table as recited in claim 9 further comprising:

a transverse overhead gripping bar.

13. The treatment table as recited in claim 9 further comprising:

an adjustable lumbar support assembly tiltable both relative to a primary plane of said body support assembly and relative to said rigid support platform.

14. The table as recited in claim 9 further comprising:

a leg support assembly transversely mounted to said rigid platform, said assembly comprising a cushion positionally adjustable relative to a plane normal to said platform and having a range extending below said plane in which the curvature of the lower body of a patient, beneath the center of gravity thereof, may be thereby regulated, whereby a variety of therapeutic effects upon the spine of a patient may be accomplished through dynamic rotation thereof off of the ground, selectable positional adjustment of said body platform relative to said base, and change in position of either or both said back assembly and said leg support assembly relative to the patient center of gravity.

15. The table as recited in claim 9 further comprising:

a leg support assembly transversely mounted to said rigid platform, said assembly comprising a cushion positionally adjustable relative to a plane normal to said platform and having a range extending below said plane in which the curvature of the lower body of a patient, beneath the center of gravity thereof, may be thereby regulated, whereby a variety of therapeutic effects upon the spine of a patient may be accomplished through dynamic rotation thereof off of the ground, selectable positional adjustment of said body platform relative to said base, and change in position of either or both said back assembly and said leg support assembly relative to the patient center of gravity.

16. The treatment table as recited in claim 1 further comprising:

means for permitting a patient to hold onto the treatment table during a dynamic rotation thereof.

17. The table as recited in claim 1 in which said system support means further comprises extensible elevation means, an upper end thereof including said pivot axis.

18. The table as recited in claim 17 further comprising:

a lumbar support assembly separated from said body support assembly; and means for independent articulation and movement of said lumbar assembly in a plane either above, below, or tilted relative to proximal portions of said body support assembly.

19. The table as recited in claim 1 in which said upper part of said rigid support platform defines a plane tilted convexly relative to plane defined by said lower part.

20. A rotatable treatment table for extension, flexion, traction, distraction, and lateral movement of the spine of a patient, the table comprising:

(a) a base adapted to rest upon a floor;

(b) system support means having an upper end and a lower end integrally secured to said base, said support means including a pivoted fulcrum proximal to said upper end thereof;

(c) means for selectable reciprocal extension having an upper end and a lower end, one end pivotally attached to said system support means, said selectable extension means providing reciprocal movement of said one end relative to an opposite end thereof;

(d) a rigid support platform having a lower end and an upper end, said platform rigidly secured to said fulcrum and, further, pivotally secured to said one end of said selectable extension means, thereby providing a resultant rotational motion of said support platform;

(e) a body support assembly adjustably positionable relative to said rigid support platform, said assembly having an upper end and a lower end; and (f) means for enabling said patient to remain on said body support assembly during rotational movement thereof, and (g) means for mechanically incrementally rotating said fulcrum and associated support platform.

21. The system as recited in claim 20 in which said body support assembly further comprises:

a contoured lumbar and buttock support in which a center of gravity of a patient is within a longitudinal dimension of said lower end of said body support assembly.

* * * * *